United States Patent [19]

Kocal

[11] Patent Number: 4,465,874
[45] Date of Patent: Aug. 14, 1984

[54] HYDRATION OF OLEFINS
[75] Inventor: Joseph A. Kocal, Waukegan, Ill.
[73] Assignee: UOP Inc., Des Plaines, Ill.
[21] Appl. No.: 455,354
[22] Filed: Jan. 3, 1983
[51] Int. Cl.$^3$ .................... C07C 29/04; C07C 31/125
[52] U.S. Cl. .................................................. 568/898
[58] Field of Search ....................................... 568/898
[56] References Cited
FOREIGN PATENT DOCUMENTS
1351492  5/1974  United Kingdom ................ 568/898

Primary Examiner—J. E. Evans
Attorney, Agent, or Firm—James R. Hoatson, Jr.; Raymond H. Nelson; William H. Page, II

[57] ABSTRACT

Olefins containing from 2 to about 6 carbon atoms may be directly hydrated by treatment with water in the presence of a catalyst comprising an alpha-zirconium phosphate. The use of this catalyst which possesses desirable thermal stability characteristics will enable the reaction to be effected at higher operating conditions than is possible when utilizing other catalysts.

3 Claims, No Drawings

HYDRATION OF OLEFINS

BACKGROUND OF THE INVENTION

Alcohols, and particularly low molecular weight alcohols, are important compounds in the chemical industry, the uses of alcohols being extremely varied in nature. For example, one of the most common alcohols, namely ethyl alcohol, may be used as a solvent or extraction medium in the manufacture of organic derivatives, dyes, synthetic drugs, rubber, detergents, cosmetics, pharmaceuticals, explosives, beverages, rocket fuels, etc. Likewise, isopropyl alcohol will find use in the manufacture of acetone, acetic anhydrides, as a solvent for essential and other oils, alkaloids, gums, resins, etc., as a latent solvent for cellulose derivatives, as an antistalling agent and deicing agent, for liquid fuels, in pharmaceuticals, perfumes, lacquers, etc. Another important article of commerce would be sec-butyl alcohol which may be used in the preparation of methyleneketone, as a solvent in varnishes, lacquers, in paint removers, etc. Inasmuch as these alcohols are important articles of commerce, it is necessary that a relatively inexpensive process or starting material is used in order to minimize the expense of using such compounds. One potential source of raw materials for the production of these low molecular weight alcohols such as ethyl alcohol or isopropyl alcohol may be found in the off-gases which are a by-product of various refinery operations in which petroleum is produced to prepare more useable products such as internal combustion engines utilizing gasoline as a fuel therefor. For example, one of the processes which is employed comprises a fluid catalytic cracking operation which is utilized to obtain gasoline which possesses a relatively high octane number.

Heretofore, mixtures of off-gases which include olefins and paraffins have formed the feedstock for preparing alcohols. However, the catalyst which has been employed in these processes comprises sulfonic acid resins. A drawback which is found when utilizing these compounds as catalysts lies in the fact that the resins usually demonstrate poor stability at reaction temperatures greater than about 150° C. In order to overcome this deficiency, it is now proposed that olefins may be subjected to a hydration reaction utilizing, as the catalyst therefor, certain compounds of a type hereinafter set forth in greater detail.

SUMMARY OF THE INVENTION

This invention relates to a process for the direct hydration of olefins to form the corresponding alcohols. More specifically, the invention is directed to a process whereby low molecular weight olefins may be directly hydrated to corresponding alcohols by treatment with water in the presence of certain catalytic compositions of matter. By utilizing the catalysts of the present invention, it will be possible to directly hydrate an olefin which possesses a relatively low molecular weight by treatment with water at reaction conditions which will insure a higher conversion of the olefins with an excellent selectivity to the desired alcohol. As hereinbefore set forth, this process is important inasmuch as low molecular weight alcohols constitute valuable articles of commerce which find a wide variety of uses in the chemical industry, specifically, and to limited industries in general.

It is therefore an object of this invention to provide a method for the direct hydration of olefinic hydrocarbons to the corresponding alcohols.

In one aspect, an object of this invention can be found in a process for the hydration of an olefinic hydrocarbon which comprises treating said hydrocarbon with water at hydration conditions in the presence of a hydration catalyst comprising an alpha-zirconium phosphate and recovering the resultant alcohol.

A specific object of this invention is found in the process for the hydration of an olefinic hydrocarbon which comprises treating propylene with water at a temperature in the range of from about 100° to about 300° C. and a pressure in the range of from about 10 to about 500 psig and a mole ratio of water to propylene in the range of from about 10:1 to about 50:1 moles of water per mole of propylene in the presence of a hydration catalyst comprising alpha-zirconium orthophosphate and recovering the resultant isopropanol.

Other objects and embodiments can be found in the following further detailed description of the present invention.

DETAILED DESCRIPTION OF THE INVENTION

As hereinbefore set forth, the present invention is concerned with a process for the hydration of olefinic hydrocarbons to prepare the corresponding alcohols. The process is effected by treating an olefinic hydrocarbon containing from about 2 to about 6 carbon atoms with water in the presence of certain catalytic compositions of matter of the type hereinafter set forth in greater detail. Examples of olefinic hydrocarbons which may be employed as the starting materials in the process of this invention will include ethylene, propylene, butene-1, butene-2, pentene-1, pentene-2, hexene-1, hexene-2, hexene-3, etc. It is also contemplated within the scope of this invention that mixtures of the aforesaid olefins such as mixtures of ethylene and propylene, propylene and butene, etc. may also be used as the starting materials. In the preferred embodiment of this invention, the olefins will comprise the off-gases from refinery operations and may include mixtures of olefins and paraffins such as ethylene/ethane or propylene/propane.

The hydration of the olefins by treatment with water is effected at hydration conditions which will include operating parameters such as temperatures in the range of from about 100° to about 300° C., pressures ranging from about 10 to about 500 pounds per square inch gauge (psig), Liquid Hourly Space Velocities ranging from about 0.1 to about 10.0 hrs.$^{-1}$ based upon the olefin charged, and water to hydrocarbon ratios ranging from about 10:1 to about 50:1 moles of water per mole of hydrocarbon.

The catalytic composition of matter which is used to effect the hydration of the olefin will comprise an alpha-zirconium phosphate, some specific examples of these compounds including alpha-zirconium orthophosphate, alpha-zirconium metaphosphate, alpha-zirconium pyrophosphate, ortho-zirconium hypophosphate, etc. The catalytic compositions of matter comprise solids which possess a layered or sheet-type structure in which the distance between the layers may be varied depending upon the preparative techniques which are employed in forming the catalyst. Various methods of preparing the catalyst may be employed including those which are well known in the art. By forming the catalyst in a layered structure and by utilizing a cross-linking agent, it is possible to obtain a catalytic composition of matter which possesses excellent thermal stability and thus may be employed to effect the desired hydration reaction at temperatures well in excess of those which have heretofore been used in hydration reactions.

The process of the present invention may be effected in any suitable manner and may comprise either a batch or continuous type of operation. For example, when a batch type operation is employed, a quantity of the catalyst is placed in an appropriate apparatus such as an autoclave of the rotating, mixing or stirring type along with water in an amount sufficient to afford the desired ratio of water to hydrocarbon. The autoclave is sealed and the hydrocarbon charge comprising an olefin containing from 2 to about 6 carbon atoms along with, if so desired, a paraffin which acts as a diluent, is charged to the reactor until the desired operating pressure has been attained. In the preferred embodiment of the invention, the operating pressure is afforded by the autogeneous pressure of the olefin, if in gaseous form. However, it is also contemplated within the scope of this invention that the olefinic charge stock may afford only a partial operating pressure, the remainder being produced by the introduction of a substantially inert gas such as nitrogen, helium, argon, etc. Upon attaining the desired operating pressure, the apparatus is heated to a predetermined operating temperature within the range hereinbefore set forth, higher operating temperatures being possible due to the heretofore stated thermal stability of the catalytic compositions of matter. After allowing the hydration reaction to proceed for a predetermined period of time which may range from about 0.5 up to about 10 hours or more in duration, the reaction time being dependent upon the operating parameters chosen, heating is discontinued. After the apparatus has returned to room temperature, the excess pressure is vented, the apparatus is opened and the reaction mixture is recovered therefrom. The liquid reaction mixture is separated from the catalyst by conventional means such as filtration, decantation, centrifugation, etc., and subjected to conventional means of separation such as fractional distillation, whereby the desired alcohol is separated from unreacted water and/or undesirable side products which may have been formed, and recovered.

It is also contemplated that the hydration reaction of the present invention may be effected in a continuous manner of operation. When such a type of operation is employed, a quantity of the catalyst is placed in an appropriate reaction apparatus which is maintained at the desired operating conditions of temperature and pressure. The olefinic charge stock and the water are continuously charged to the reactor through separate means and, after passage through the reactor for a predetermined period of time, the reactor effluent is continuously withdrawn. The effluent is then subjected to conventional means of separation whereby unreacted starting materials comprising the olefinic hydrocarbon and water are separated from the alcohol product and recycled to the reaction zone to form a portion of the feedstock, while the desired product is recovered.

A continuous type of operation may be effected in any suitable manner, one type of operation comprising a fixed bed mode in which the catalytic composition of matter is positioned in the reactor as a fixed bed and the reactants are passed through said bed in either an upward or downward flow. Alternatively, a moving bed type of operation may be employed in which the catalyst and the reactants are passed through the reaction zone either concurrently or countercurrently to each other. A third method of operation which may be employed comprises the slurry type of operation in which the catalytic composition of matter is charged to the reactor as a slurry in either the water or the olefinic hydrocarbon.

Examples of alcohols which may be produced by utilizing the process of this invention will include ethanol, isopropanol, sec-butanol, sec-pentanol and sec-hexanol.

The following examples are given for purposes of illustrating the process of this invention. However, it is to be understood that these examples are given merely for purposes of illustration and that the present process is not necessarily limited thereto.

EXAMPLE I

Isopropanol may be prepared by placing the catalytic composition of matter comprising alpha-zirconium orthophosphate in a rotating autoclave along with a sufficient amount of water necessary to maintain a ratio of 25:1 moles of water per mole of hydrocarbon. The autoclave may then be sealed at a 65/35 mixture of propylene/propane charged thereto until a pressure of 100 psig is attained. The autoclave may then be heated to a temperature of 200° C. and maintained thereat for a period of four hours. At the end of this period, heating may be discontinued and after the autoclave has returned to room temperature, the excess pressure may be vented. The autoclave may then be opened and the reaction mixture recovered therefrom. After separating the liquid mixture from the catalyst, the former may then be subjected to fractional distillation and the desired isopropanol may be recovered therefrom.

EXAMPLE II

In this example, a catalyst comprising alpha-zirconium metaphosphate may be placed in an autoclave along with water in an amount sufficient so as to maintain a mole ratio of 50 moles of water per mole of hydrocarbon which may be charged to the reactor. The autoclave may then be sealed and a mixture of butene-2 and butane may be charged to the reactor until an initial operating pressure of 250 psig has been reached. The autoclave may then be heated to a temperature of 300° C. and maintained thereat for a period of four hours. At the end of this time, heating may be discontinued and, after the autoclave has reached room temperature, the excess pressure may be vented. The autoclave may then be opened and the reaction mixture recovered therefrom. After separation from the catalyst, the liquid reaction mixture may again be subjected to fractional distillation and the desired sec-butanol may be separated from water and recovered.

EXAMPLE III

In a manner similar to that hereinbefore set forth, alpha-zirconium pyrophosphate may be used to catalyze the hydration of pentene-2 and hexene-1 by treating these compounds at an elevated temperature of about 250° C. and a pressure of 500 psig for a period of four hours. After recovery of the liquid product and separation from the catalyst, the product may be subjected to fractional distillation and the desired sec-pentanol and sec-hexanol recovered therefrom.

I claim as my invention:

1. A process for the preparation of an alcohol by the hydration of an olefinic hydrocarbon selected from the group consisting of pentene-1, pentene-2, hexene-1, hexene-2 and hexene-3, which comprises treating said olefinic hydrocarbon with water at a temperature in the range of from about 100° to about 300° C., a pressure in the range of from about 10 to about 500 pounds per square inch gauge and a molar ratio of water to olefinic hydrocarbon in a range of from about 10:1 to about 50:1 moles of water per mole of hydrocarbon in the presence of a hydration catalyst selected from the group consisting of alpha-zirconium metaphosphate, alpha-zirconium pyrophosphate and ortho-zirconium hypophosphate to produce the resultant alcohol, which is recovered.

2. The process as set forth in claim 1 in which said olefinic hydrocarbon is pentene and said alcohol is sec-pentanol-2.

3. The process as set forth in claim 1 in which said olefinic hydrocarbon is hexene-1 and said alcohol is sec-hexanol.

* * * * *